(12) United States Patent
Ren et al.

(10) Patent No.: US 10,408,601 B2
(45) Date of Patent: Sep. 10, 2019

(54) VISUALIZATION SYSTEMS AND METHODS FOR OPTIMIZED OPTICAL COHERENCE TOMOGRAPHY

(71) Applicant: Novartis AG, Basel (CH)

(72) Inventors: Hugang Ren, Cypress, CA (US); Lingfeng Yu, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/808,070

(22) Filed: Nov. 9, 2017

(65) Prior Publication Data

US 2018/0149467 A1    May 31, 2018

Related U.S. Application Data

(60) Provisional application No. 62/428,318, filed on Nov. 30, 2016.

(51) Int. Cl.
| | | |
|---|---|---|
| *G01B 9/02* | (2006.01) | |
| *A61B 3/10* | (2006.01) | |
| *A61B 3/14* | (2006.01) | |
| *A61B 3/00* | (2006.01) | |
| *A61B 3/15* | (2006.01) | |
| *G01J 9/02* | (2006.01) | |

(52) U.S. Cl.
CPC ........ *G01B 9/02091* (2013.01); *A61B 3/0083* (2013.01); *A61B 3/102* (2013.01); *A61B 3/14* (2013.01); *A61B 3/152* (2013.01); *G01J 2009/0269* (2013.01)

(58) Field of Classification Search
CPC ......... A61B 3/102; A61B 3/14; A61B 5/0066; A61B 5/0073; G01B 9/02091; G02B 27/40; G03B 13/36
See application file for complete search history.

(56) References Cited

U.S. PATENT DOCUMENTS

| | | | | |
|---|---|---|---|---|
| 2004/0113043 | A1* | 6/2004 | Ishikawa | G02B 21/245 |
| | | | | 250/201.4 |
| 2010/0033811 | A1* | 2/2010 | Westphal | G02B 7/36 |
| | | | | 359/368 |
| 2011/0299034 | A1* | 12/2011 | Walsh | A61B 3/102 |
| | | | | 351/206 |
| 2012/0069303 | A1 | 3/2012 | Seesselberg et al. | |
| 2013/0162978 | A1* | 6/2013 | Yazdanfar | G01B 9/02064 |
| | | | | 356/51 |
| 2013/0265545 | A1 | 10/2013 | Buckland et al. | |
| 2015/0272435 | A1* | 10/2015 | Ito | A61B 3/102 |
| | | | | 351/206 |

(Continued)

FOREIGN PATENT DOCUMENTS

| | | |
|---|---|---|
| DE | 102011119899 A1 | 6/2013 |
| DE | 202014011051 U1 | 7/2017 |

(Continued)

*Primary Examiner* — Michael P LaPage

(57) ABSTRACT

The present disclosure provides a visualization system for performing optimized optical coherence tomography (OCT) by determining the absolute distance between the OCT source and a sample. The present disclosure also provides a method for optimizing OCT, which includes determining an absolute distance between the OCT source and a sample using data relating to the focal length or position of an autofocus imager lens.

7 Claims, 4 Drawing Sheets

(56) References Cited

U.S. PATENT DOCUMENTS

2015/0293340 A1* 10/2015 Cable .................. G02B 21/245
    359/370
2015/0294458 A1* 10/2015 Biernat ................ A61B 3/0058
    382/131

FOREIGN PATENT DOCUMENTS

EP          2965688 A1    1/2016
WO       2015166695 A1   11/2015

* cited by examiner

VISUALIZATION SYSTEMS AND METHODS FOR OPTIMIZED OPTICAL COHERENCE TOMOGRAPHY

TECHNICAL FIELD

The disclosure relates to optical coherence tomography (OCT), and more specifically, to visualization systems and methods for optimized OCT scanning.

BACKGROUND

Eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. During ophthalmic surgery, a patient is placed on a support, facing upward. The support may a couch or a bed and may be positioned under a surgical microscope. An eye speculum is inserted to keep the eye exposed. Surgeons often use the surgical microscope to view the patient's eye, and surgical instruments may be introduced to perform any of a variety of different procedures. The surgical microscope provides imaging and optionally illumination of parts of the eye during the procedure.

In addition to simply allowing a close-up view of the eye, a surgical microscope may be equipped with an OCT system to provide additional information about internal structures of the eye that cannot effectively be seen using only the surgical microscope. OCT systems may be optically or electro-mechanically integrated into the surgical microscope.

OCT is an interferometric analysis technique for structural examination of a sample that is at least partially reflective to light, for example, a biological tissue. OCT can also be used for functional examination of a sample, such as the motion and velocity of the sample or blood flow in a tissue. OCT systems may be used to determine distance and depth profiles and other information based on interference patterns created by the interaction between a reflected beam from a reference mirror and a reflected beam from a sample.

In an OCT system, a single OCT source beam is split into two component beams, a sample beam that is propagated to and at least partially reflected by a sample, and a reference beam that is propagated to and reflected by a reference mirror. Each beam is typically reflected back to the beam splitter and combined, although certain OCT systems may not require each reflected beam to return to the beam splitter to be combined. When the reflected sample beam and reflected reference beam are combined, an interference pattern is generated, which may be used to measure distances and depth profiles of the sample and other information and to image internal target structures that the sample beam passed through. In ophthalmic surgery, an OCT system may be used, for example, to provide cross sectional views of the retina in high resolution.

SUMMARY

The present disclosure provides a visualization system that includes an OCT system with an OCT source that is operable to generate an OCT source beam, an OCT beam splitter, and an OCT detector. The OCT beam splitter is operable to split the OCT source beam into a sample beam that travels along a sample arm until it is reflected by a sample to form a reflected sample beam, and a reference beam that travels along a reference arm until it is reflected by a reference mirror in the OCT system to form a reflected reference beam, and operable to combine the reflected sample beam and the reflected reference beam to form a reflected OCT beam. The OCT detector is operable to receive the reflected OCT beam and operable to detect an interference pattern of the reflected OCT beam. The visualization system also includes a surgical microscope, a dichroic mirror operable to allow non-OCT light to substantially pass through and operable to reflect the sample beam, and a visualization beam splitter operable to direct non-OCT light into both the surgical microscope and an autofocus imager. The autofocus imager is operable to receive non-OCT light reflected by the sample that has passed through the dichroic mirror and has been directed by the visualization beam splitter to the autofocus imager. The autofocus imager is operable to use the non-OCT light reflected by the sample to optimize the focus of the autofocus imager on the sample by adjusting an autofocus imager lens, and is operable to generate data relating to a position or a focal length of the autofocus imager lens. The visualization system further includes a processor operable to determine a distance between the dichroic mirror and the sample using the data relating to the position or the focal length of the autofocus imager lens, determine an absolute distance between the OCT source and the sample using the distance between the dichroic mirror and the sample, determine a length of the sample arm using the absolute distance between the OCT source and the sample, generate a control signal operable to optimize the OCT system by adjusting the length of the reference arm or the focus of the sample arm, and transmit the control signal to the OCT system.

In additional embodiments, which may be combined with one another unless clearly exclusive: the autofocus imager lens is a power adjustable lens, and a focal length of the power adjustable lens is adjusted; the autofocus imager lens is a position adjustable lens, and a position of the position adjustable lens is adjusted; the processor is operable to calculate the length of the sample arm, using the absolute distance between the OCT source and the sample, generate and transmit the control signal in real time; the processor is operable to determine the absolute distance between the OCT source and the sample by reference to lens-distance reference data; and the lens-distance reference data includes data corresponding to the distance between the OCT source and the sample at different focal lengths or positions of the autofocus imager lens.

The present disclosure further provides a visualization system that includes an OCT system with an OCT source that is operable to generate an OCT source beam, an OCT beam splitter, and an OCT detector. The OCT beam splitter is operable to split the OCT source beam into a sample beam that travels along a sample arm until it is reflected by a sample to form a reflected sample beam, and a reference beam that travels along a reference arm until it is reflected by a reference mirror in the OCT system to form a reflected reference beam, and operable to combine the reflected sample beam and the reflected reference beam to form a reflected OCT beam. The OCT detector is operable to receive the reflected OCT beam and operable to detect an interference pattern of the reflected OCT beam. The visualization system also includes a surgical microscope, a dichroic mirror operable to allow non-OCT light to substantially pass through and operable to reflect the sample beam, and a visualization beam splitter operable to direct non-OCT light into both the surgical microscope and an autofocus imager. The autofocus imager is operable to receive non-OCT light reflected by the sample that has passed through the dichroic mirror and has been directed by the visualization beam splitter to the autofocus imager. The autofocus imager is operable to use the non-OCT light reflected by the sample to optimize the focus of the autofocus imager on the sample by adjusting an autofocus imager lens, and is operable to generate data relating to a position or a focal length of the autofocus imager lens.

The visualization system further includes a processor operable to determine a change in distance between the dichroic mirror and the sample using the data relating to the position or the focal length of the autofocus imager lens, determine a change in the length of the sample arm using the change in distance between the dichroic mirror and the sample, generate a control signal operable to optimize the OCT system by adjusting the length of the reference arm or the focus of the sample arm, and transmit the control signal to the OCT system.

In additional embodiments, which may be combined with one another unless clearly exclusive: the autofocus imager lens is a power adjustable lens, and a focal length of the power adjustable lens is adjusted; the autofocus imager lens is a position adjustable lens, and a position of the position adjustable lens is adjusted; and the processor is operable to determine the change in the length of the sample arm using the change in distance between the dichroic mirror and the sample, generate and transmit the control signal in real time.

The disclosure also provides a method for optimizing optical coherence tomography (OCT) that includes receiving, at an autofocus imager, non-OCT light reflected by a sample, the non-OCT light having passed through a dichroic mirror and having been directed by a visualization beam splitter to the autofocus imager, using the non-OCT light reflected by the sample, at the autofocus imager, to optimize the focus of the autofocus imager on the sample by adjusting an autofocus imager lens, generating data, by the autofocus imager, relating to a position or a focal length of the autofocus imager lens, determining a distance between the dichroic mirror and the sample using the data relating to the position or the focal length of the autofocus imager lens, determining an absolute distance between the OCT source and the sample using the distance between the dichroic mirror and the sample, determining a length of the sample arm using the absolute distance between the OCT source and the sample, generating a control signal, the control signal operable to optimize the OCT system by adjusting the length of the reference arm or the focus of the sample arm, and transmitting the control signal to the OCT system.

In additional embodiments, which may be combined with one another unless clearly exclusive: the lens of the autofocus imager is a power adjustable lens, and the control device is operable to adjust the focal length of the lens; the lens of the autofocus imager is a position adjustable lens, and the control device is operable to adjust the position of the lens; calculating the length of the sample arm, using the absolute distance between the OCT source and the sample, and generating and transmitting the control signal is in real time; determining an absolute distance between the OCT source and the sample is by reference to lens-distance reference data; and wherein the lens-distance reference data includes data corresponding to the distance between the OCT source and the sample at different focal lengths or positions of the autofocus imager lens.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not drawn to scale, and in which.

DETAILED DESCRIPTION

Figure 1:
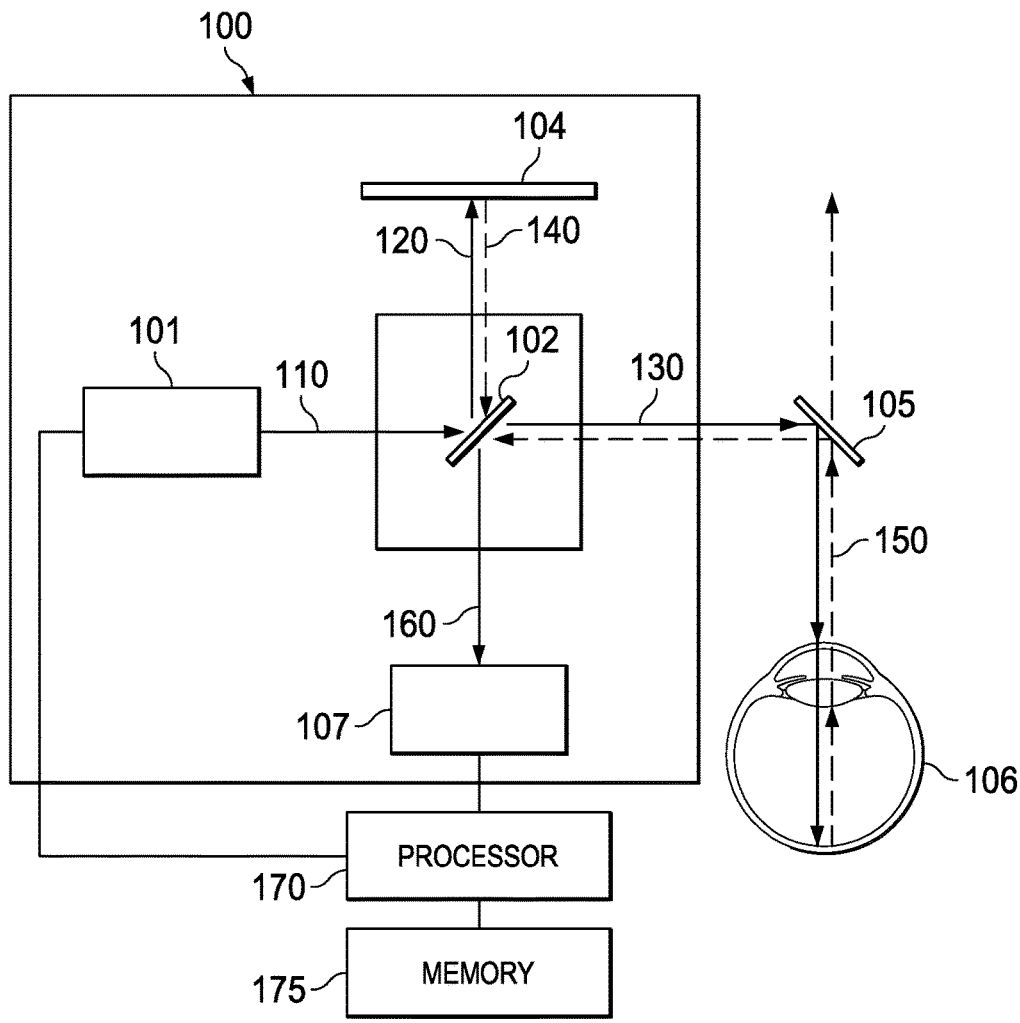
FIG. 1 is a schematic representation of an OCT system.

In the following description, details are set forth by way of example to facilitate discussion of the disclosed subject matter. It should be apparent to a person of ordinary skill in the field, however, that the disclosed embodiments are exemplary and not exhaustive of all possible embodiments.

When performing OCT, it is important to obtain an analyzable interference pattern to allow for proper measurements and imaging of internal target structures the sample beam passed through. To obtain such an interference pattern, it is important to minimize any difference between the length of the reference arm and the length of the sample arm. Preferably, any such difference in length is insubstantial and any variance is known. For example, the difference between the length of the reference arm and the length of the sample arm may be considered insubstantial when it is less than 100 mm. In an OCT system, the length of the reference arm refers to the distance between the OCT beam splitter and the reference mirror. The length of the sample arm refers to the distance between the OCT beam splitter and the sample. At present, adjustments to the length of the reference arm or sample arm are performed manually.

In typical use of an OCT system, a user may manually adjust the position of the OCT source back and forth until the length of the reference arm and the sample arm are the same, and an optimal image is obtained. However, in certain instances, it may not be possible or practicable to move the OCT source back and forth to get an optimal image, for example, when an OCT system is connected to a surgical microscope. In such instances, a user may be more concerned with getting a clear surgical microscope view during surgery than obtaining an optimized OCT image. In order to obtain a clear surgical microscope view, the user may adjust the focus of the surgical microscope or move the surgical microscope up or down, which alters the position of the OCT source and as a result, the length of the sample arm. To maintain an optimized OCT image, the length of the reference arm must be adjusted as the focus or position of the surgical microscope is adjusted.

The disclosure provides a visualization system that incorporates an autofocus imager, which may generate data relating to a position or a focal length of the autofocus imager lens. The autofocus imager lens may be, for example, a power adjustable lens in which the focal length of the lens may be adjusted, or a position adjustable lens in which the position of the lens may be adjusted. By implementing an autofocus imager, the visualization systems herein provide automated adjustment of the length of the reference arm or the focus of the sample arm, as compared to manual adjustment by a user.

A processor of the visualization system determines the distance between the dichroic mirror and the sample using the data relating to the position or the focal length of the autofocus imager lens. The processor determines the absolute distance between the OCT source and the sample using the distance between the dichroic mirror and the sample. The processor further determines the length of the sample arm using the absolute distance between the OCT source and the sample. By making these determinations, the visualization system can optimize OCT scanning, by adjusting the length of the reference arm, the focus of the sample arm, or both. The length of the reference arm may be adjusted, for example, via a control device connected to the reference mirror. The focus of the sample arm may be adjusted by either adjusting a position of an OCT lens, of the OCT system, or the focus of the OCT lens. The OCT lens, though not included in FIG. 1, may be at any position between the beam splitter and the sample, which as shown, is any position on path 130 or 150, as described further below in reference to FIG. 1. By adjusting the length of the reference arm, the focus of the sample arm, or both, the visualization systems perform optimized OCT scanning, which results in an interference pattern that is more analyzable, and accordingly, an optimized OCT image.

Referring now to the drawings, FIG. 1 is a schematic representation of an OCT system 100, which, as shown, includes a scanning mirror 105. OCT system 100 is connected to a processor 170, which is connected to memory 155. OCT system 100 includes OCT beam splitter 102, detector 107, reference mirror 104, and OCT source 101. OCT source 101 generates an OCT source beam, which is propagated on path 110 toward OCT beam splitter 102. OCT beam splitter 102 splits the OCT source beam propagated on path 110 into two component beams: (1) a sample beam that is propagated along a sample arm, path 130, to a sample 106, after being reflected off scanning mirror 105; and (2) a reference beam that is propagated along a reference arm, path 120, to reference mirror 104. Sample 106 may be, for example, a patient's eye.

Once the sample beam reaches sample 106, it is reflected back toward OCT beam splitter 102 on path 150. OCT beam splitter 102 combines the reflected sample beam, on path 140, and the reflected reference beam, on path 150, to create an interference pattern. The combined reflected beams are called a "reflected OCT beam."

The reflected OCT beam is directed to detector 107. Detector 107 may be, for example, a photodetector. Detector 107 detects the interference pattern of the reflected OCT beam and generates data relating to the interference pattern. Processor 170 receives the data from detector 107 and may process the data to generate an OCT image of internal target structures that the sample beam passed through.

A processor 170 may include, for example a microprocessor, microcontroller, digital signal processor (DSP), application specific integrated circuit (ASIC), or any other digital or analog circuitry configured to interpret and/or execute program instructions and/or process data. In some embodiments, processor 170 may interpret and/or execute program instructions and/or process data stored in memory 175. Memory 175 may be configured in part or whole as application memory, system memory, or both. Memory 175 may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 2:
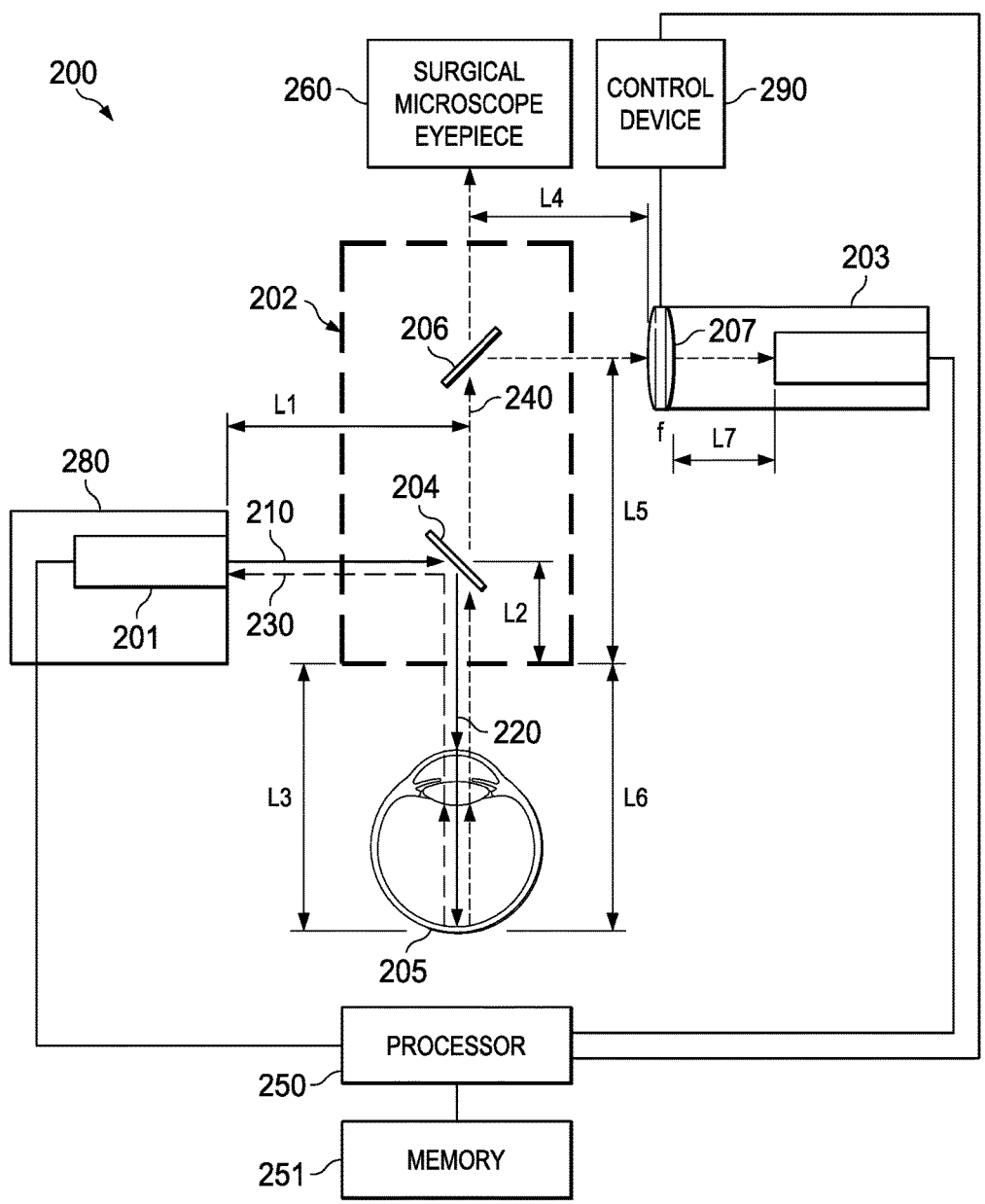
FIG. 2 a schematic representation of a visualization system that includes an OCT system and an autofocus imager with a power adjustable lens.

FIG. 2 is a schematic representation of a visualization system 200 that includes an autofocus imager 203 with a power adjustable lens 207. Power adjustable lens 207 may be incorporated into autofocus imager 203 or connected to it. Power adjustable lens 207 is connected to a control device 290, which can adjust at least the focal length of the power adjustable lens. Adjusting the focal length of power adjustable lens 207 may be referred to as adjusting the "power" of the power adjustable lens. Visualization system 200 also includes surgical microscope 202 with a surgical microscope eyepiece 260, processor 250, memory 251, dichroic mirror 204, visualization beam splitter 206, and OCT system 280. OCT system 280 includes an OCT source 201, an OCT beam splitter, a reference mirror, a detector, and an OCT lens.

Visualization system 200 optimizes the resulting interference pattern, and accordingly, the resulting OCT image, by performing optimized OCT scanning. To perform optimized OCT scanning, visualization system 200 may adjust the length of the reference arm or the focus of the sample arm, of the OCT system. As discussed for FIG. 2, the reference arm and the sample arm relate to the OCT system 280, not visualization system 200. The focus of the sample arm may be adjusted by either adjusting a position of the OCT lens, or the focus of the OCT lens. As described above, although not shown in FIG. 2, the OCT lens may be at any position between the OCT beam splitter, of OCT system 280, and sample 205.

OCT source 201 generates an OCT source beam, which is propagated on path 210 toward dichroic mirror 204. Dichroic mirror 204 may be incorporated into surgical microscope 202. Dichroic mirror 204 directs the OCT source beam toward sample 205, along path 220. Sample 205 may be a patient's eye. Once the OCT source beam on paths 210 and 220 reaches sample 205, it is reflected back toward dichroic mirror 204 and directed back to OCT system 280, on path 230.

Dichroic mirror 204 is a mirror that has significantly different reflection or transmission properties at two different wavelengths. Such properties allow the dichroic mirror to reflect the OCT source beam, which is generally near the infrared range and generally higher than a 700 nm wavelength. In contrast, such properties also allow the dichroic mirror to transmit non-OCT light, which is in the visible range and generally less than a 700 nm wavelength. For example, non-OCT light may be ambient light or light generated by the surgical microscope.

While the OCT source beam is being directed along paths 210 and 220, autofocus imager 203 receives non-OCT light reflected by the sample that has passed through the dichroic mirror and has been directed by the visualization beam splitter to the autofocus imager. Autofocus imager 203 receives this non-OCT light through its power adjustable lens 207. Autofocus imager 203 can detect and generate data relating to the focal length and the position of power adjustable lens 207. The non-OCT light, on path 240, may be for example, ambient light or light generated by the surgical microscope. On path 240, the transmitted non-OCT light passes through dichroic mirror 204 and is split into two component beams at visualization beam splitter 206.

Visualization beam splitter 206 is a part of the surgical microscope 202. Visualization beam splitter 206 splits the beam of non-OCT light, and directs one component beam to the autofocus imager lens 207 and the other component beam to the eyepiece of the surgical microscope 260 so that the user can observe the sample 205.

Once autofocus imager 203 receives the autofocus beam, it can optimize the focus of power adjustable lens 207 on the sample by adjusting at least the focus of power adjustable lens 207. Autofocus imager 203 may use the non-OCT light to optimize the focus of the autofocus imager on the sample by adjusting power adjustable lens 207. Autofocus imager 203 can detect and generate data relating to the focal length or position of power adjustable lens 207.

Processor 250 can receive the data relating to the focal length and position of power adjustable lens 207 and process it to determine the distance between dichroic mirror 204 and the sample 205. Processor 250 can determine the absolute distance between the OCT source and sample 205, using the distance between the dichroic mirror and the sample. Processor 250 can further determine the length of the sample arm using the absolute distance between the OCT source and the sample.

Alternatively, processor 250 may determine the change in distance between dichroic mirror 204 and the sample 205 using the data relating to the position or the focal length of the autofocus imager lens. Processor 250 may further determine the change in the length of the sample arm using the change in distance between the dichroic mirror and the sample. In this example, processor 250 may still adjust the reference arm and focus of the sample arm to optimize the OCT system: (1) without determining or using the determination of the distance between the dichroic mirror and the sample; or (2) without determining or using the determination of the absolute distance between the OCT source and the sample. Instead, processor 250 may determine any change in distance between the dichroic mirror and the sample, determine a change in the length of the sample arm, and use that determination to optimize the OCT system.

Processor 250 may generate a control signal to optimize the OCT system 280 by adjusting the length of the reference arm or the focus of the sample arm, and transmit the control signal to the OCT system 280. The length of the reference arm may be adjusted, for example, via a control device. The focus of the sample arm may be adjusted by either adjusting the position of an OCT lens, of the OCT system, or the focus of the OCT lens. By adjusting the length of the reference arm or the focus of the sample arm, any difference between the lengths of the reference arm and the sample arm may be minimized, and preferably insubstantial. By minimizing any difference between the lengths of the reference arm and the sample arm, the visualization system optimizes the resulting interference pattern and accordingly, the resulting OCT image.

In the visualization system of FIG. 2, the length of the "sample arm" is the distance from OCT source 201 to the sample 205, which equals L1+L2+L3, where L1 is the distance between OCT source 201 and dichroic mirror 204, L2 is the distance between dichroic mirror 204 and the edge of surgical microscope 202, and L3 is the distance between the edge of surgical microscope 202 and sample 205. L1 and L2 are fixed. The only variable parameter in the calculation of the length of the sample arm is L3, the changing distance between surgical microscope 202 and sample 205.

In FIG. 2, the length of the "object distance" is the distance from the power adjustable lens 207 to the sample 205, which equals L4+L5+L6, where L4 is the distance between the power adjustable lens 207 and visualization beam splitter 206, L5 is the distance between visualization beam splitter 206 and the edge of surgical microscope 202, and L6 is the distance between the edge of surgical microscope 202 and the sample 205. As shown, L3 and L6 are the same distance. The distance between power adjustable lens 207 and a sensor of the autofocus imager 203 is shown as L7.

In visualization system 200, $$\frac{1}{f} = \frac{1}{(L4+L5+L6)} + \frac{1}{L7}$$

in which "f" represents the focal length of power adjustable lens 207. This equation may be solved for L6 as follows:

$$L6 = \frac{fL7}{L7-f} - L4 - L5$$

As stated above and shown in FIG. 2, L6=L3. As a result, the absolute distance between OCT source 201 and the sample 205, designated $L_{OCT}$, can be calculated as:

$$L_{OCT} = L1 + L2 + L3 = L1 + L2 + \frac{fL7}{L7-f} - L4 - L5$$

Of the parameters in the above equation, L1, L2, L7, L4, and L5 are properties of the visualization system, as configured. Focal length "f" may be displayed or determined by autofocus imager 203. From there, $L_{OCT}$ may be determined by processor 250.

As described above, $L_{OCT}$, the absolute distance between OCT source 201 and the sample 205, is determined using the distance between the dichroic mirror and the sample, which is determined using the data relating to the position or the focal length of the autofocus imager lens. In this example, the autofocus imager lens is power adjustable lens 207. Processor 250 determines a length of the sample arm using the absolute distance between the OCT source and the sample, and generates a control signal to adjust either the position of an OCT lens or the focus of the OCT lens to minimize any difference between the lengths of the reference arm and the sample arm, which optimizes OCT scanning.

Figure 3:
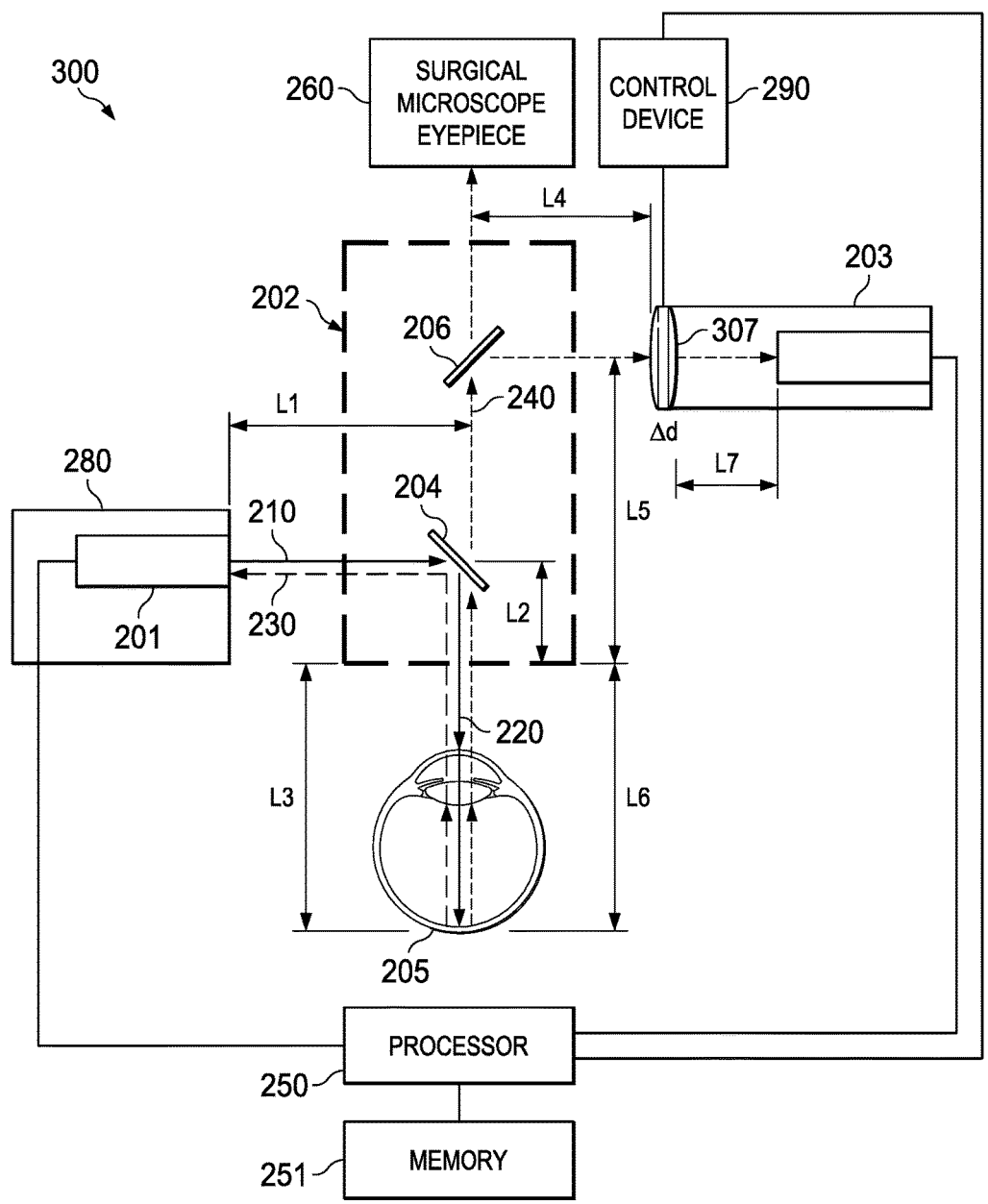
FIG. 3 is a schematic representation of a visualization system that includes an OCT system and an autofocus imager with a position adjustable lens.

FIG. 3 is a schematic representation of a visualization system 300 that includes an autofocus imager 203 with a position adjustable lens 307, in contrast to the power adjustable lens 207 of visualization system 200. Autofocus imager 203 may optimize its focus on the sample by adjusting a position of position adjustable lens 307. Position adjustable lens 307 may be incorporated into autofocus imager 203 or connected to it. Position adjustable lens 307 is connected to a control device 290, which can adjust at least the position of the position adjustable lens. Visualization system 200 also includes surgical microscope 202 with a surgical microscope eyepiece 260, processor 250, memory 251, dichroic mirror 204, visualization beam splitter 206, and OCT system 280. OCT system 280 includes an OCT source 201, an OCT beam splitter, a reference mirror, a detector, and an OCT lens.

Visualization system 200 optimizes the resulting interference pattern, and accordingly, the resulting OCT image, by performing optimized OCT scanning. To perform optimized OCT scanning, visualization system 200 may adjust the length of the reference arm or the focus of the sample arm, of the OCT system. As discussed for FIG. 2, the reference arm and the sample arm relate to the OCT system 280, not visualization system 200. The focus of the sample arm may be adjusted by either adjusting a position of the OCT lens, or the focus of the OCT lens. As described above, although not shown in FIG. 2, the OCT lens may be at any position between the OCT beam splitter, of OCT system 280, and sample 205.

OCT source 201 generates an OCT source beam, which is propagated on path 210 toward dichroic mirror 204. Dichroic mirror 204 may be incorporated into surgical microscope 202. Dichroic mirror 204 directs the OCT source beam toward sample 205, along path 220. Sample 205 may be a patient's eye. Once the OCT source beam on paths 210 and 220 reaches sample 205, it is reflected back toward dichroic mirror 204 and directed back to OCT system 280, on path 230.

While the OCT source beam is being directed along paths 210 and 220, autofocus imager 203 receives non-OCT light reflected by the sample that has passed through the dichroic mirror and has been directed by the visualization beam splitter to the autofocus imager. In contrast to visualization system 200 of FIG. 2, in visualization system 300 of FIG. 3, autofocus imager 203 receives this non-OCT light through its power adjustable lens 207. Autofocus imager 203 can detect and generate data relating to the focal length and the position of power adjustable lens 207. The non-OCT light, on path 240, may be for example, ambient light or light generated by the surgical microscope. On path 240, the transmitted non-OCT light passes through dichroic mirror 204 and is split into two component beams at visualization beam splitter 206.

Visualization beam splitter 206 is a part of the surgical microscope 202. Visualization beam splitter 206 splits the beam of non-OCT light, and directs one component beam to the autofocus imager lens 307 and the other component beam to eyepiece of the surgical microscope 260 so that the user can observe the sample 205.

Once autofocus imager 203 receives the autofocus beam, it can optimize the focus of position adjustable lens 307 on the sample by adjusting at least the position of position adjustable lens 307. Autofocus imager 203 may use the non-OCT light to optimize the focus of the autofocus imager on the sample by adjusting position adjustable lens 307. Autofocus imager 203 can detect and generate data relating to the focal length or position of position adjustable lens 307.

Processor 250 can receive the data relating to the focal length and position of position adjustable lens 307 and process it to determine the distance between dichroic mirror 204 and the sample 205. Processor 250 can determine the absolute distance between the OCT source and sample 205, using the distance between the dichroic mirror and the sample. Processor 250 can further determine the length of the sample arm using the absolute distance between the OCT source and the sample.

Alternatively, processor 250 may determine the change in distance between dichroic mirror 204 and the sample 205 using the data relating to the position or the focal length of the autofocus imager lens. Processor 250 may further determine the change in the length of the sample arm using the change in distance between the dichroic mirror and the sample. In this example, processor 250 may still adjust the reference arm and focus of the sample arm to optimize the OCT system: (1) without determining or using the determination of the distance between the dichroic mirror and the sample; or (2) without determining or using the determination of the absolute distance between the OCT source and the sample. Instead, processor 250 may determine any change in distance between the dichroic mirror and the sample, determine a change in the length of the sample arm, and use that determination to optimize the OCT system.

Processor 250 may generate a control signal to optimize the OCT system 280 by adjusting the length of the reference arm or the focus of the sample arm, and transmit the control signal to OCT system 280. The length of the reference arm may be adjusted, for example, via a control device. The focus of the sample arm may be adjusted by either adjusting the position of an OCT lens, of the OCT system, or the focus of the OCT lens. By adjusting the length of the reference arm or the focus of the sample arm, any difference between the lengths of the reference arm and the sample arm may be minimized, and preferably insubstantial. By minimizing any difference between the lengths of the reference arm and the sample arm, the visualization system optimizes the resulting interference pattern and accordingly, the resulting OCT image.

In the visualization system of FIG. 3, the length of the "sample arm" is the distance from OCT source 201 to the sample 205, which equals L1+L2+L3, where L1 is the distance between OCT source 201 and dichroic mirror 204, L2 is the distance between dichroic mirror 204 and the edge of surgical microscope 202, and L3 is the distance between the edge of surgical microscope 202 and sample 205. L1 and L2 are fixed. The only variable parameter in the calculation of the length of the sample arm is L3, the changing distance between surgical microscope 202 and sample 205.

In FIG. 3, the length of the "object distance" is the distance from the position adjustable lens 307 to the sample 205, which equals L4+L5+L6, where L4 is the distance between the position adjustable lens 307 and visualization beam splitter 206, L5 is the distance between visualization beam splitter 206 and the edge of surgical microscope 202, and L6 is the distance between the edge of surgical microscope 202 and the sample 205. As shown, L3 and L6 are the same distance. In contrast to visualization system 200 of FIG. 2, the distance between position adjustable lens 307 and a sensor of the autofocus imager 203 is shown as L7.

In visualization system 300, $$\frac{1}{f} = \frac{1}{(L4+L5+L6+\Delta d)} + \frac{1}{L7-\Delta d}$$

in which "f" represents the focal length of position adjustable lens 307. This equation may be solved for L6 as follows:

$$L6 = \frac{f(L7-\Delta d)}{L7-\Delta d-f} - L4 - L5 - \Delta d$$

As stated above and shown in FIG. 2, L6=L3. As a result, the absolute distance between OCT source 201 and the sample 205, designated $L_{OCT}$, can be calculated as:

$$L_{OCT} = L1 + L2 + L3 = L1 + L2 + \frac{f(L7 - \Delta d)}{L7 - \Delta d - f} - L4 - L5 - \Delta d$$

Of the parameters in the above equation, L1, L2, L7, L4, and L5 are properties of the visualization system, as configured. Focal length "f" is fixed in this situation because position adjustable lens 307 is implemented, as opposed to power adjustable lens 207, and Δd can be read from the display on autofocus imager 203. From there, $L_{OCT}$ may be determined by processor 250.

As described above, $L_{OCT}$, the absolute distance between OCT source 201 and the sample 205, is determined using the distance between the dichroic mirror and the sample, which is determined using the data relating to the position or the focal length of the autofocus imager lens. In this example, the autofocus imager lens is position adjustable lens 307. Processor 250 determines a length of the sample arm using the absolute distance between the OCT source and the sample, and generates a control signal to adjust either the position of an OCT lens or the focus of the OCT lens to minimize any difference between the lengths of the reference arm and the sample arm, of the OCT system, which optimizes OCT scanning.

Visualization system 200 of FIG. 2 or any component thereof may be used with visualization system 300 of FIG. 3 or any component thereof, and vice versa.

For both visualization systems 200 and 300, calculating the length of the sample arm, using the absolute distance between the OCT source and the sample, and generating and transmitting the control signal may be performed in real time. Real time may mean in less than half a second, in less than one second, or otherwise in less than the normal reaction time of a user of the visual information. Also, determining $L_{OCT}$, the absolute distance between the OCT source and the sample, may be performed by reference to lens-distance reference data. The lens-distance reference data may include data corresponding to the distance between the OCT source and the sample at different focal lengths or positions of the autofocus imager lens.

Figure 4:
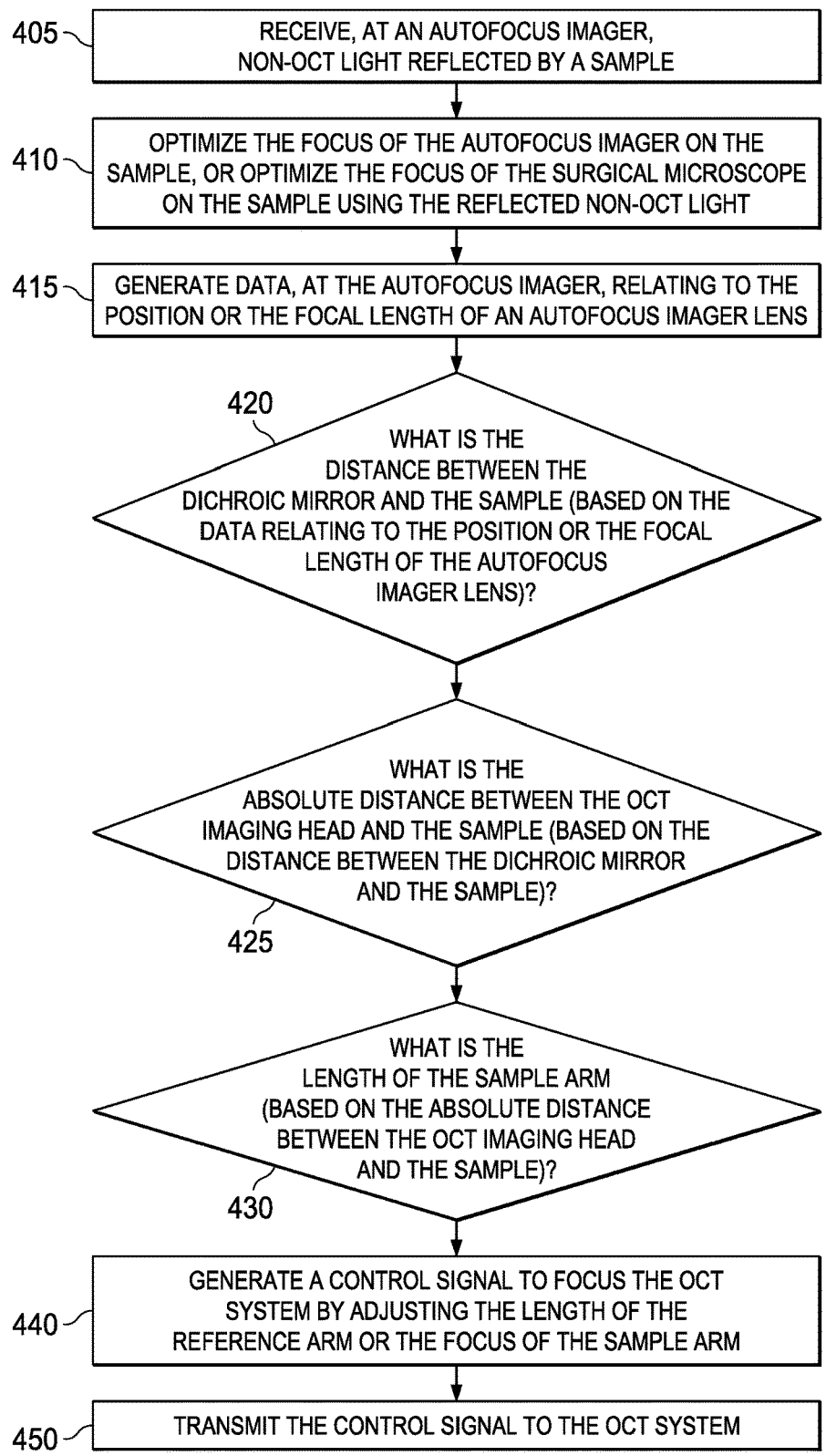
FIG. 4 is a flowchart of a method for optimizing OCT.

FIG. 4 is a flowchart of a method for optimizing OCT. At step 405 non-OCT light, reflected by a sample, is received at an autofocus imager. The sample may be, for example, a patient's eye. Non-OCT light may be, for example, ambient light or light generated by the surgical microscope. At step 410, the focus of the autofocus imager on the sample is optimized, using the non-OCT light reflected from the sample.

At step 415, data is generated, at the autofocus imager, relating to the position or the focal length of an autofocus imager lens. The data generated may include any change in position or focal length of the autofocus imager lens, the change caused when the focus of the autofocus imager on the sample is optimized, using the non-OCT light reflected from the sample. The autofocus imager lens may be, for example, a position adjustable lens (as described in FIG. 3) or a power adjustable lens (as described in FIG. 2). The data generated may include only the position of the autofocus imager lens, if a position adjustable lens is implemented and only the position of the position adjustable lens is adjusted. In contrast, if a power adjustable lens is implemented, the data received should include the focal length and the position of the power adjustable lens.

At step 420, the distance between the dichroic mirror and the sample may be determined based on the data relating to the position or the focal length of the autofocus imager lens.

At step 425, $L_{OCT}$, the absolute distance between the OCT source and the sample, may be determined as described in FIG. 2 for a visualization system with a power adjustable lens or as described in FIG. 3 for a visualization system with a position adjustable lens. At step 430, the length of the sample arm, of the OCT system, may be determined, based on the absolute distance between the OCT source and the sample.

Alternatively to steps 420, 425, and 430, the change in distance between the dichroic mirror and the sample may be determined, using the data relating to the position or the focal length of the autofocus imager lens, and the change in the length of the sample arm may be determined, using the change in distance between the dichroic mirror and the sample. In this example, the OCT system may still be optimized by adjusting the reference arm or focus of the sample arm: (1) without determining or using the determination of the distance between the dichroic mirror and the sample; or (2) without determining or using the determination of the absolute distance between the OCT source and the sample. Instead, any change in distance between the dichroic mirror and the sample is determined, and any change in the length of the sample arm is determined and used to optimize the OCT system.

At step 440, a control signal may be generated to optimize the OCT system by adjusting the length of the reference arm, the focus of the sample arm, or both. The length of the reference arm may be adjusted, for example, via a control device connected to the reference mirror of the OCT system. The focus of the sample arm may be adjusted by either adjusting a position of an OCT lens, of the OCT system, or the focus of the OCT lens.

At step 450, the control signal may be transmitted to the OCT system to adjust either the length of the reference arm, the focus of the sample arm, or both. By performing such adjustments, the OCT performance is optimized because any difference between the length of the reference arm and the length of the sample arm is minimized. Preferably, any such difference in length is made insubstantial and any variance is known. For example, the difference between the length of the reference arm and the length of the sample arm may be considered insubstantial when it is less than 100 mm. This results in an interference pattern that is more analyzable, and accordingly, an optimized OCT image.

Method 400 may be implemented using the visualization systems of FIG. 2 or FIG. 3, or any other suitable system. The preferred initialization point for such methods and the order of their steps may depend on the implementation chosen. In some embodiments, some steps may be optionally omitted, repeated, or combined. In some embodiments, some steps of such methods may be executed in parallel with other steps. In certain embodiments, the methods may be implemented partially or fully in software embodied in computer-readable media.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such wires, optical fibers, and other electromagnetic and/or optical carriers; and/or any combination of the foregoing.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A visualization system comprising:
an OCT system comprising
an OCT source operable to generate an OCT source beam;
an OCT beam splitter operable to split the OCT source beam into a sample beam that travels along a sample arm until it is reflected by a sample to form a reflected sample beam, and a reference beam that travels along a reference arm until it is reflected by a reference mirror in the OCT system to form a reflected reference beam, and operable to combine the reflected sample beam and the reflected reference beam to form a reflected OCT beam; and
an OCT detector operable to receive the reflected OCT beam and operable to detect an interference pattern of the reflected OCT beam;
a surgical microscope;
a dichroic mirror operable to allow non-OCT light to substantially pass through and operable to reflect the sample beam; and
a visualization beam splitter operable to direct non-OCT light into both the surgical microscope and;
an autofocus imager, the autofocus imager operable to:
receive non-OCT light reflected by the sample that has passed through the dichroic mirror and an autofocus imager lens, and
generate data relating to a position and a focal length of the autofocus imager lens; and
a processor operable to:
determine a distance between the dichroic mirror and the sample using the data relating to the position and the focal length of the autofocus imager lens;
determine an absolute distance between the OCT source and the sample using the distance between the dichroic mirror and the sample;
determine a length of the sample arm using the absolute distance between the OCT source and the sample;
generate a control signal operable to optimize the OCT system by adjusting the length of the reference arm or the focus of the sample arm; and
transmit the control signal to the OCT system.

2. The visualization system of claim 1, wherein the autofocus imager lens is a power adjustable lens, and wherein a focal length of the power adjustable lens is adjusted.

3. The visualization system of claim 1, wherein the autofocus imager lens is a position adjustable lens, and wherein a position of the position adjustable lens is adjusted.

4. The visualization system of claim 1, wherein the processor is operable to:
calculate the length of the sample arm, using the absolute distance between the OCT source and the sample; and
generate and transmit the control signal in real time.

5. The visualization system of claim 1, wherein the processor is operable to determine the absolute distance between the OCT source and the sample by reference to lens-distance reference data.

6. The visualization system of claim 5, wherein the lens-distance reference data includes data corresponding to the distance between the OCT source and the sample at different focal lengths or positions of the autofocus imager lens.

7. The visualization system of claim 1 wherein the autofocus imager lens is selected from the group consisting of: a power adjustable lens and a position adjustable lens.

* * * * *